United States Patent [19]

de Gaston

[11] 4,048,507

[45] Sept. 13, 1977

[54] X-RAY BEAM PERPENDICULAR FINDER

[76] Inventor: Alexis Neal de Gaston, 2190 Santa Anita Road, Norco, Calif., 91760

[21] Appl. No.: 657,164

[22] Filed: Feb. 11, 1976

[51] Int. Cl.² ............................................. G03B 41/16
[52] U.S. Cl. ..................................... 250/491; 250/476
[58] Field of Search ......................... 250/476, 491, 312

[56] References Cited
U.S. PATENT DOCUMENTS

| | | | |
|---|---|---|---|
| 3,547,121 | 12/1970 | Cherry | 250/476 |
| 3,577,160 | 5/1971 | White | 250/476 |
| 3,928,767 | 12/1975 | Roeck | 250/476 |

*Primary Examiner*—Craig E. Church
*Attorney, Agent, or Firm*—George W. Finch

[57] ABSTRACT

A pair of separated semi-radio opaque sheets having a similar target pattern removed therefrom are placed in parallel alignment with the targets in perpendicular alignment. When exposed to an X-ray beam of a diagnostic X-ray machine, the targets produce a pattern in the radiograph in which the two targets are superimposed in slight misalignment except where the X-ray beam is perpendicular, thereby locating the perpendicular X-ray beam position with respect to the collimator jaws and visual target of the machine.

8 Claims, 5 Drawing Figures

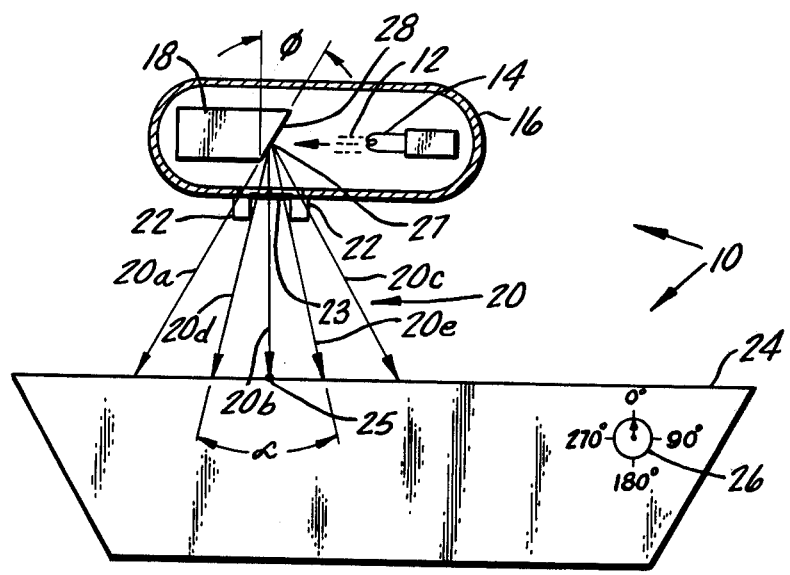
FIG_1
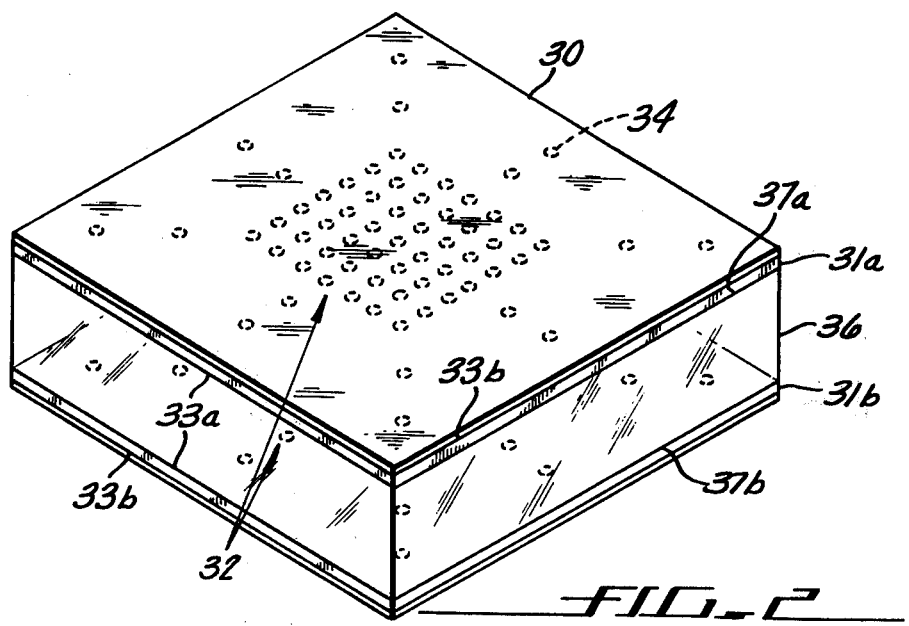
FIG_2
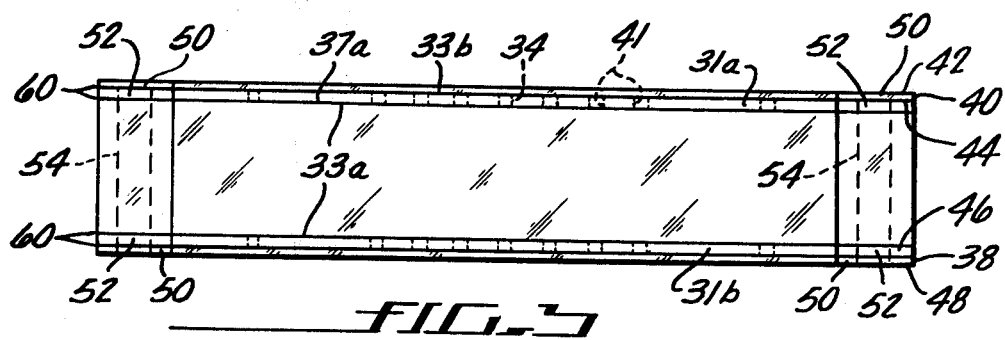
FIG_3

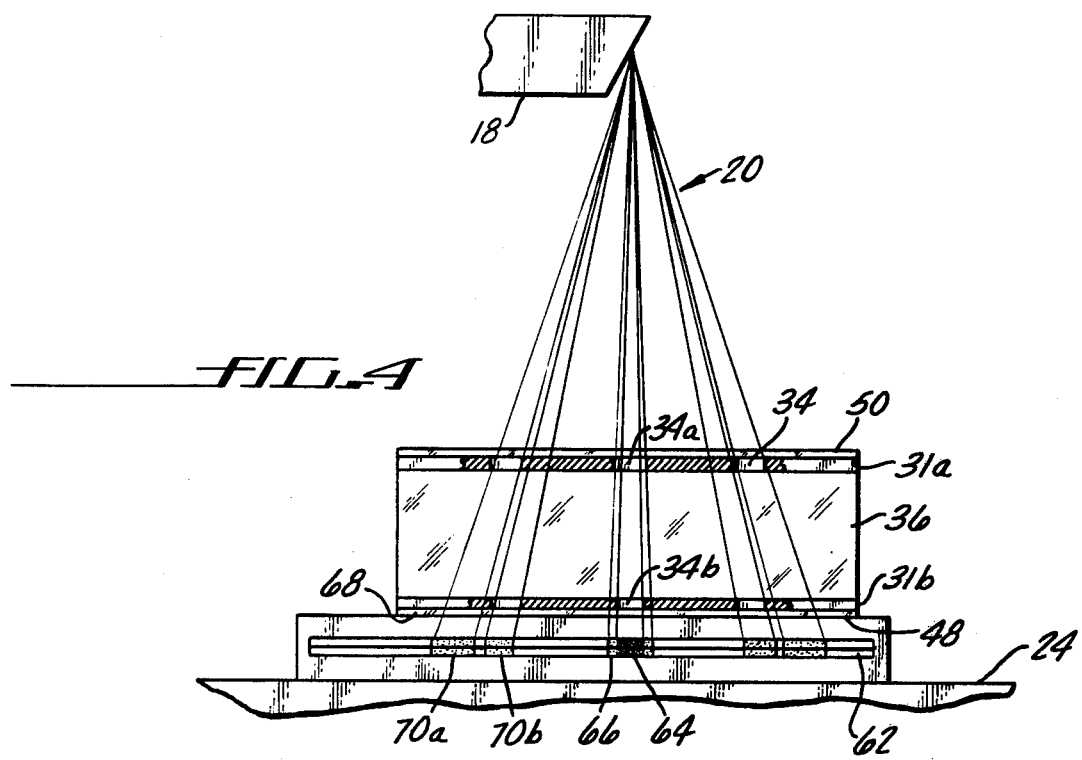
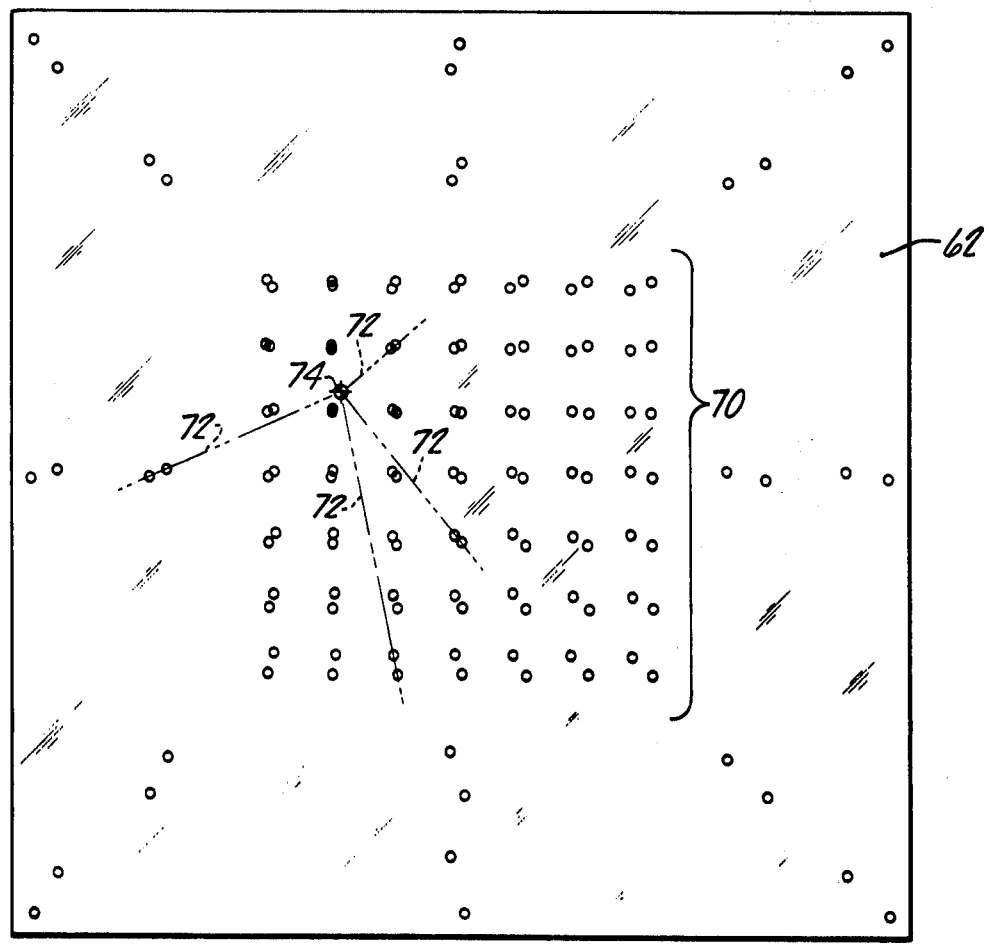

X-RAY BEAM PERPENDICULAR FINDER

BACKGROUND OF THE INVENTION

As the standard quality demanded in X-radiography increases, it is imperative that quality control methods and devices be instituted to assure conformance with newly developed standards. For example, it is desirable that the center of the X-ray beam in a diagnostic X-ray machine be perpendicular at its center since anything else results in inconsistent radiographs of the same patient from machine to machine or, if the perpendicular is varying, on the same machine at two different times. This lack of consistency whether it be location, shading or intensity makes the diagnosis of a slowly progressing illness difficult for the doctor and sometimes results in incorrect diagnosis. Heretofore, wire cage devices have been used with X-ray machines to form a target which when radiographed can be used to crudely indicate the angular relationship of the X-ray beam at the indicated center thereof. These wire cage devices are disadvantageous since the wire therein must be small and fragile to produce any useful result. They also produce radiographs of low resolution due to the varying effective thickness of the wires to the X-rays. It is therefore difficult to determine exactly the perpendicular of the X-ray beam. The wire cage devices are relatively expensive to make and being fragile, they must be repaired or replaced at regular intervals.

It should be mentioned that newer X-ray standards also require that anode focal spot measurements be obtained, a project that is extremely difficult if the beam is not perpendicular at the spot indicated to be its center by the visual cross hair shadow target, a feature provided in most X-ray machines.

BRIEF SUMMARY OF THE INVENTION

The present invention solves the problems of the prior art targets and allows a quantum jump in resolution and hence, accuracy, when determining the angular relationship of an X-ray beam. The device, which can be constructed in many forms, usually includes two flat, thin plates of semi-radio opaque material through which a pattern of exactly registered circular holes of a predetermined diameter have been formed. The plates are spaced perpendicularly a known distance by a frame or a solid nonradio opaque material such as plastic while their registry is maintained.

The center of the patterns are placed at the location on the table of the X-ray machine which is indicated as the center of the X-ray field by the projection of a visible cross-hair target. If the X-ray tube is properly installed, this center is directly below the focal spot on the X-ray tube anode. A radiograph of the present device is then taken. The alignment of the X-ray beam can be determined easily by comparing the patterns produced by the two radio opaque plates on the radiograph and observing the misregistries thereof.

It is therefore an object of the present invention to provide improved means for determining the angular relationship of the X-ray field of a diagnostic X-ray machine.

Another object is to improve the diagnostic quality of X-ray machines by providing means which enable their calibration within predetermined limits.

Another object is to provide means for finding an X-ray beam perpendicular which are relatively rugged, easy and economical to manufacture and are quickly and easily usable in the hurried environment of a hospital.

Another object is to provide means which enable more accurate, repeatable focal spot pictures of an X-ray tube.

These and other objects and advantages of the present invention will become apparent to those skilled in the art after considering the following detailed specification which covers a preferred embodiment thereof in conjunction with the accompanying drawings wherein:

BRIEF DESCRIPTION OF THE DRAWINGS

FIG. 1 is a diagrammatic view of a typical diagnostic X-ray machine;

FIG. 2 is an isometric view of the device of the present invention showing a preferred target pattern therein;

FIG. 3 is a side view of the device of FIG. 2 showing it before a final step of manufacture;

FIG. 4 is an exaggerated diagrammatic view of the present device in operation determining the angular relationship of the center of an X-ray field; and FIG. 5 is a representation of an actual radiograph taken with the present device in the beam and indicating a misalignment of the X-ray machine.

DETAILED DESCRIPTION OF THE SHOWN EMBODIMENT

Referring to the drawings more particularly by reference numbers, number 10 in FIG. 1 refers to a diagnostic X-ray machine typical of those used for diagnostic and treatment purposes at the present time. The machine 10 operates by directing an electron beam 12 from the filament 14 in an X-ray tube 16 toward an anode 18 at energies high enough to generate X-radiation 20, shown for illustrative purposes as rays 20a, 20b, 20c, 20d, and 20e. The X-rays are normally contained in a predetermined field of view by means of collimator jaws 22 which operate somewhat like the iris of a camera. Means 23 are usually included to produce a visual indication of the field and its center 25. The X-rays 20 are directed toward the patient table 24 on which the patient is normally placed. In most modern X-ray machines 18 this table 24 can be tilted to various angles and some means are provided such as the tilt indicator 26 to indicate the tilt thereof. When the anode and the visual center indicator means 23 are properly aligned, the beam 20 should have a field of view between ray 20d and 20e and be centered and perpendicular to the table 24 set at a 0° tilt. The angle between rays 20d and 20e as determined by the positions of the collimator jaws 22 is named α in FIG. 1. When the jaws 22 and visual indication means are misaligned in the direction of ray 20a, a larger portion of the X-ray energy is reduced by self-absorbtion in the anode 18. This is commonly called "heel effect" and can reduce the desired exposure to a point that makes diagnosis impossible and treatment also ineffectual. The problems attendant with heel effect are well-known in the art.

Reduced resolution is the result if there is misalignment in the direction of ray 20c. To understand this one must understand the physical relationship of the anode 18 with respect to the beam of electrons 12. The angle $\phi$ from perpendicular to the face of the anode 18 is normally an optimization and tradeoff between heel effect and focal spot size, the focal spot 27 being the effective area of the anode face 28 struck by the beam 12 of electrons at any instant. The angle $\phi$ is typically 16° to 17½° and the small angle results in a relatively small apparent focal spot size looking up from the table 24 due to a foreshortening effect. It should be obvious that looking back into the anode 18 from the table 24 along ray 20c, more of the anode would be visible and therefore a larger apparent focal spot 27. In the ideal case, the focal spot 27 of the X-ray machine should be a point source but this is never the case.

Therefore, if the collimator jaws 22 are misaligned toward ray 20a, a decrease in X-ray emission of the tube 16 passing therethrough results in underexposures whereas beams misaligned in the direction of ray 20c result in poor resolution due to effective focal spot size increase. Since both off perpendicular positionings of the X-ray field grossly effect the quality of X-radiographs, it is imperative that easy quality control methods and devices be available to assure performance conformance from machine to machine and from day to day so that doctors can properly diagnose and treat their patients.

A preferred embodiment of the present alignment device 30 is shown in FIGS. 2 and 3 essentially as it was described in disclosure No. 038907 submitted to the Document Disclosure Officer, U.S. Patent and Trademark Office on 18 Feb., 1975. In the following description various dimensions and numbers are used primarily for illustrative purposes and are not to be construed as limiting the invention. It should be noted also that semi-radio opaque and nonradio opaque are meant to be relative and not absolute terms.

The device 30 includes a pair of semi-radio opaque sheets 31a and 31b preferably having an identical target pattern 32 cut therethrough. Typical sheets are of copper, steel or other easily obtainable metal. The preferable target pattern 32 is made up of a multiplicity of circular holes 34 which are of identical size and placement on both sheets 31a and 31b. The sheets 31a and 31b which have parallel inside and outside surfaces 33a and 33b are held in alignment with the targets 32 in perpendicular resolution by suitable means such as a nonradio opaque block 36 which has parallel sides 37a and 37b. The block 36 can be made out of any convenient, physically stable material such as high grade plastic. As shown in FIG. 3, thin sheets 38 and 40 of nonradio opaque material having parallel sides 42 and 44, 46 and 48 can be attached to the outside surfaces 33b of the plates 31a and 31b to protect them from physical damage.

In constructing the device 30, it is convenient to place the two sheets 31a and 31b in contact and then by means of removable tabs 50, hold them while the holes 34 are cut therethrough. Alignment holes 52 of a diameter large enough to allow structural support, are usually included in the tabs 50 so that once the holes 34 are formed, a jig having perpendicular pins which fit in the holes 52 and in similar holes 54 in the block 36 can be used to assure the alignment of the plates 31a and 31b. In the manufacturing process, the cover sheets 38 and 40 are placed over the sheets 31a and 31b and the tabs are removed once suitable adhesive 60 assures that the sheets 31a and 31b cannot move with respect to the block 36. It should be noted that the holes 34 are defined by cylindrical surfaces 41 which are perpendicular to the sheets.

The device 30 is shown in use in FIG. 4. Assuming that the holes 34a and 34b have been placed at the center position indicated by the visual means 23, the X-rays 20 are shown emitting from the anode 18 in the correct perpendicular fashion with respect to the table 24. These X-rays 20 pass through the holes 34 in the plates 31a and 31b to produce images in a film 62 positioned on the X-ray table 24. It is apparent that the central pair of holes 34a and 34b are centered on the perpendicular. If the focal distance from the anode 18 to the film 62 is 100 centimeters, the distance between the copper sheets is 5 centimeters and the hole diameters are one millimeter, then the image 64 of the bottom hole 34b will be approximately 1 millimeter in diameter and the image 66 of the upper hole 34a will be 1.053 millimeters in diameter plus penumbral blur. The penumbral blur for a 1 millimeter focal spot is 0.06 millimeters if the bottom 68 of the device 30 is 1 centimeter from the film 62. Thus the effective image diameter of the upper hole 34a will be about 1.11 millimeter or 10% larger than the image diameter of the lower hole 34b. Concentricity of the images 64 and 66 on the film 62 can be determined within better than 0.1 millimeters which results in the determination of the alignment of the center of X-ray beam 20 to 1 part in 500 or an angle of less than 7 minutes of arc. This is 2 millimeters at 100 centimeters.

Alignment is less finely determinable by looking at the array of developed images 70 on the exposed film 62 which are shown in FIG. 5. As is illustrated in FIG. 5, lines 72 drawn from the centers of the larger images 70a through the centers of the paired smaller images 70b when extended intersect beneath the perpendicular showing the immediate position 74 where the perpendicular was located.

The use of the invention 30 extends beyond the alignment described above to another important facet in image quality control. The inherent resolution capability or radiography is limited by the focal spot size and intensity distribution. For uniformity the focal spot is defined as measured at the perpendicular position and this requirement is adopted into the National Electrical Manufacturing Association Standards. The present invention allows the location of the perpendicular with high accuracy, an essential element for correct focal spot measurement. Once the perpendicular of the spot is located, a pinhole camera or other device may be placed therealong and aligned to enable correct focal spot pictures to thereby determine apparent focal spot size and intensity distribution. If the apparent focal spot is smaller than specified by the manufacturer, a misalignment of the anode and the collimator jaws 22 in the direction of ray 20a (FIG. 1) is indicated and if the apparent focal spot size is larger than specified then misalignment therebetween toward ray 20c is indicated.

Thus there has been shown and described a novel device for enabling the perpendicular alignment of the center of the X-ray field of an X-ray machine with respect to its table which fulfills all of the objects and advantages sought therefor. Many changes, modifications, variations, and other uses and applications of the subject invention will, however, become apparent to those skilled in the art after considering this specification together with the accompanying drawings. All such changes, modifications, variations and other uses and applications which do not depart from the spirit and scope of the invention are deemed to be covered by the invention which is limited only by the claims which follow.

What is claimed is:

1. A device for finding the location of the perpendicular ray of an X-ray beam field including:

first and second semi-radio opaque layers each defining a pattern therethrough removed therefrom, said pattern being defined by cutouts formed with edges perpendicular to said semi-radio opaque layers; and means to space and maintain said first and second semi-radio opaque layers in parallel alignment with their pattern in perpendicular registry, said means including a nonradio opaque member having parallel sides to which said layers are attached.

2. The device defined in Claim 1 wherein said patterns are defined by a plurality of cylindrical surfaces which pass through said layers in perpendicular alignment therewith.

3. The device defined in claim 1 wherein said cutouts through said semi-radio opaque layers are formed with said layers in surface to surface contact so that the pattern so formed is identical, said layers also having at least two cylindrical alignment pin surfaces which pass therethrough in perpendicular alignment therewith, said alignment pin surfaces being formed when said layers are in surface to surface contact so that the pattern can be exactly aligned on said nonradio opaque member.

4. The device defined in claim 1 including two sheets of nonradio opaque material, said sheets each having parallel side surfaces one of which is attached to one of said layers on the opposite side thereof from said member.

5. A process for locating the perpendicular ray of an X-ray beam field with respect to the location indicated to be the center of the field by an X-ray machine including the steps of:

placing a device having first and second semiradio opaque sheets each having a protective nonradio opaque parallel surface layer on one surface thereof, a similar plurality of portions removed therethrough to define a pattern and means to space and maintain said first and second semi-radio opaque sheets in parallel alignment with their patterns in perpendicular registry including a block having parallel sides to which said sheets are connected on the opposite sides thereof from said protective layers, said block being constructed from a material allowing easier passage of X-rays than the material from which said sheets are constructed, in a known position with respect to the indicated center of the field;

exposing a medium sensitive to X-rays through said device by producing an X-ray beam with the X-ray machine; and comparing the positions of the misalignments of said patterns, lines through registered portions of said patterns intersecting at the location of said perpendicular ray.

6. The process defined in Claim 5 including the additional step of:

orienting a pinhole camera upward toward the source of said X-ray beams along the perpendicular ray indicated by the comparison of the positions of misalignments of said patterns;

exposing a film sensitive to X-rays in said camera; and comparing said apparent focal spot size recorded with the X-ray machine specified apparent focal spot size to indicate the alignment of the X-ray beam source with the means which indicate the center of said X-ray beam field.

7. The process defined in claim 5 including:

adjusting said X-ray machine in accordance with said observation; and repeating the steps in order until the visually indicated center and the actual center of the X-ray beam field coinside.

8. The process defined in claim 5 wherein said patterns are defined by a plurality of cylindrical surfaces which pass between the opposite side surfaces of said sheets in perpendicular alignment thereto, said plurality of cylindrical surfaces being established in alignment by being formed when said sheets are in surface to surface contact along with at least two cylindrical alignment surfaces also perpendicular to said sheets, whereby said alignment surfaces are used to assure alignment of said plurality of cylindrical surfaces where said sheets are connected to said block.

* * * * *